(12) United States Patent
Lazennec et al.

(10) Patent No.: US 8,529,633 B2
(45) Date of Patent: Sep. 10, 2013

(54) COTYLOID IMPLANT FOR A HIP PROSTHESIS

(75) Inventors: Jean-Yves Lazennec, L'Hay-les-Roses (FR); Christiane Cruchet-Boucher, Le Mans (FR)

(73) Assignee: Ceram Concept LLC, Newark, DE (US)

( * ) Notice: Subject to any disclaimer, the term of this patent is extended or adjusted under 35 U.S.C. 154(b) by 272 days.

(21) Appl. No.: 10/541,680

(22) PCT Filed: Jan. 9, 2004

(86) PCT No.: PCT/FR2004/000037
§ 371 (c)(1),
(2), (4) Date: Mar. 10, 2006

(87) PCT Pub. No.: WO2004/069091
PCT Pub. Date: Aug. 19, 2004

(65) Prior Publication Data
US 2006/0167556 A1    Jul. 27, 2006

(30) Foreign Application Priority Data

Jan. 10, 2003 (FR) ...................... 03 00059

(51) Int. Cl.
*A61F 2/32* (2006.01)
(52) U.S. Cl.
USPC ...................................... 623/22.24
(58) Field of Classification Search
USPC .......................... 623/22.11–23.63
See application file for complete search history.

(56) References Cited

U.S. PATENT DOCUMENTS

| | | | | |
|---|---|---|---|---|
| 4,437,193 A | * | 3/1984 | Oh ............................. | 623/22.24 |
| 4,563,778 A | * | 1/1986 | Roche et al. ................ | 623/22.38 |
| 4,566,138 A | * | 1/1986 | Lewis et al. ................. | 623/22.38 |
| 4,624,674 A | * | 11/1986 | Pappas et al. .............. | 623/22.19 |
| 4,642,123 A | * | 2/1987 | Noiles ......................... | 623/22.2 |
| 4,650,491 A | * | 3/1987 | Parchinski ................. | 623/22.28 |
| 4,662,891 A | * | 5/1987 | Noiles ........................ | 623/22.31 |
| 4,666,450 A | * | 5/1987 | Kenna ........................ | 623/22.28 |
| 4,676,798 A | * | 6/1987 | Noiles ........................ | 623/22.18 |
| 4,681,589 A | * | 7/1987 | Tronzo ....................... | 623/22.32 |

(Continued)

FOREIGN PATENT DOCUMENTS

| | | |
|---|---|---|
| EP | 0 091 315 | 10/1983 |
| EP | 0 773 007 | 5/1997 |

(Continued)

OTHER PUBLICATIONS

Willmann et al., "Keramische Pfanneneinsatze fur Huftendoprothesen" Biomedizinische Technik, vol. 41, No. 4, Apr. 1, 1996, XP 000583024, pp. 98-105.

*Primary Examiner* — David Isabella
*Assistant Examiner* — Ann Schillinger
(74) *Attorney, Agent, or Firm* — Young & Thompson (57) ABSTRACT

A cotyloid implant for a hip prosthesis, includes a first type of insert (2) with a spherical internal cavity (2a), for the mounting of a hemispherical core (4) with a capacity for mobility which has an internal cavity (4a) for co-operation with articulation with a femoral head, a second type of insert with an internal cavity for cooperation with a femoral head with articulation, characterized in that the center of rotation of the femoral head is different from the axis of rotation of the first type of insert (2) and/or of the second type of insert.

15 Claims, 8 Drawing Sheets

(56) References Cited

U.S. PATENT DOCUMENTS

| | | | | |
|---|---|---|---|---|
| 4,715,860 A | * | 12/1987 | Amstutz et al. | 623/22.33 |
| 4,770,661 A | * | 9/1988 | Oh | 623/22.2 |
| 4,798,610 A | * | 1/1989 | Averill et al. | 623/22.2 |
| 4,801,301 A | * | 1/1989 | Noiles | 623/22.18 |
| 4,883,490 A | * | 11/1989 | Oh | 623/22.39 |
| 4,904,265 A | * | 2/1990 | MacCollum et al. | 623/22.28 |
| 4,960,427 A | * | 10/1990 | Noiles | 623/22.18 |
| 4,978,356 A | * | 12/1990 | Noiles | 623/23.4 |
| 5,002,577 A | * | 3/1991 | Bolesky et al. | 623/22.25 |
| 5,049,158 A | * | 9/1991 | Engelhardt et al. | 623/22.25 |
| 5,080,678 A | * | 1/1992 | Spotorno et al. | 623/22.25 |
| 5,092,898 A | * | 3/1992 | Bekki et al. | 623/22.16 |
| 5,156,626 A | * | 10/1992 | Broderick et al. | 623/22.12 |
| 5,163,961 A | * | 11/1992 | Harwin | 623/22.46 |
| 5,171,285 A | * | 12/1992 | Broderick | 623/22.25 |
| 5,226,917 A | * | 7/1993 | Schryver | 623/22.37 |
| 5,314,491 A | * | 5/1994 | Thongpreda et al. | 623/22.29 |
| 5,314,494 A | * | 5/1994 | Huiskes et al. | 623/23.35 |
| 5,425,778 A | * | 6/1995 | Zichner et al. | 623/22.29 |
| 5,507,824 A | * | 4/1996 | Lennox | 623/22.25 |
| 5,507,826 A | * | 4/1996 | Besselink et al. | 623/22.29 |
| 5,725,591 A | * | 3/1998 | DeCarlo et al. | 623/22.29 |
| 5,879,398 A | * | 3/1999 | Swarts et al. | 623/22.21 |
| 5,879,401 A | * | 3/1999 | Besemer et al. | 623/22.28 |
| 5,989,293 A | * | 11/1999 | Cook et al. | 623/22.29 |
| 5,989,294 A | * | 11/1999 | Marlow | 623/22.16 |
| 6,248,132 B1 | * | 6/2001 | Harris | 623/22.15 |
| 6,328,764 B1 | * | 12/2001 | Mady | 623/22.16 |
| 6,527,808 B1 | * | 3/2003 | Albertorio et al. | 623/22.26 |
| 6,527,809 B1 | * | 3/2003 | Doursounian et al. | 623/22.28 |
| 6,610,097 B2 | * | 8/2003 | Serbousek et al. | 623/22.24 |
| 2001/0051831 A1 | * | 12/2001 | Subba Rao et al. | 623/22.42 |
| 2002/0116068 A1 | | 8/2002 | McLean | |
| 2003/0105529 A1 | * | 6/2003 | Synder et al. | 623/22.24 |
| 2003/0171817 A1 | * | 9/2003 | Rambert et al. | 623/22.17 |
| 2004/0054418 A1 | * | 3/2004 | McLean et al. | 623/22.17 |
| 2004/0225369 A1 | * | 11/2004 | Lakin et al. | 623/22.15 |

FOREIGN PATENT DOCUMENTS

| | | |
|---|---|---|
| EP | 0821922 A1 | 2/1998 |
| EP | 1 133 958 | 9/2001 |
| EP | 1 195 149 | 4/2002 |
| FR | 2700945 A3 | 8/1994 |
| FR | 2 793 137 | 11/2000 |
| FR | 2 795 302 | 12/2000 |
| FR | 2 827 154 | 1/2003 |
| GB | 2152386 A | 8/1985 |
| WO | 9727827 | 8/1997 |
| WO | WO 00/64383 | 11/2000 |
| WO | WO 02/09615 | 2/2002 |

* cited by examiner

COTYLOID IMPLANT FOR A HIP PROSTHESIS

This is a 371 National Stage application of International application no. PCT/FR2004/00037, filed Jan. 9, 2004, which claims priority to French application no. 03/00059, filed Jan. 10, 2003. The entire contents of the above-referenced applications are hereby incorporated by reference in their entirety.

The invention relates to the technical sector of orthopaedic implants for the hip joint.

BACKGROUND OF THE INVENTION

An acetabular implant essentially comprises a metallic cup with a generally hemispherical shape that will be impacted in the acetabular cavity of the iliac bone, in different arrangements, in combination or not in combination with cement. In general, the cup receives a polyethylene, ceramic or metal kernel that will cooperate with a femoral head of a complementary femoral implant, while maintaining an articulation capability. The kernel may be implanted in the internal cavity of the cup, either in a fixed manner or with a displacement or multidirectional capability.

Obviously, different arrangements will have to be made depending on the nature of the kernel (mobile or fixed with respect to the metallic cup). In other words, it is impossible to use the same metallic cup for the assembly of a mobile kernel and for the assembly of a fixed kernel.

For example, consider the information given in patent FR 2 795 302 that describes an acetabular implant comprising a cup that can hold a fixed insert or a mobile insert fixed onto a mobile kernel, while a mobile insert holds a fixed kernel. The solution described in this patent enables only the assembly of a kernel with freedom to move or the assembly of a kernel fixed to an insert mounted with freedom to move in the hemispherical cavity of the cup. The result is that the kernel cooperating with this femoral head is always free to move with respect to the cup.

SUMMARY OF THE INVENTION

Starting from this state of the art, the problem that arises and that the invention is intended to solve is to be able to use the same metallic cup depending on the type of arthroplasty to be treated, and to obtain double mobility (mobile kernel—mobile head) or single mobility (fixed insert—mobile head), remembering that in all cases the femoral head is installed with an articulation capability relative to the kernel of the acetabular implant.

An acetabular implant has been developed for a hip prosthesis to solve this type of problem, remarkable in that it comprises:
  a first type of insert has a spherical internal cavity for the assembly of a hemispherical kernel with an internal cavity capable of cooperating with a femoral head with freedom to move, and with an articulation capability;
  a second type of insert with an internal cavity capable of cooperating with the femoral head, with an articulation capability;
  characterised in that the centre of rotation of the femoral head is different from the axis of rotation of the above mentioned first type of insert and/or the above mentioned second type of insert.

Thus, the centres of rotation of the first type of insert, the second type of insert and the femoral head are aligned but are not coincident.

According to this invention, this task is solved by providing a bipolar cup between the head and the acetabulum, so that the head can rotate in the bipolar cup and the bipolar cup can rotate in the acetabular cavity. This double rotation possibility significantly reduces luxations and sub-luxations. This system is also qualified as a double mobility system or a tripolar system.

According to one embodiment of the invention described below and shown in the attached figures, the implant according to the invention will include a metallic hemispherical shaped cup that can be fixed in the bottom of the acetabular cavity of the iliac bone.

Advantageously, the above mentioned cup will delimit an internal cavity with arrangements for assembly at will, in a fixed manner, of the two above mentioned first and second insert types.

Considering these arrangements, the result is that the first type of insert can provide a means of obtaining double mobility (mobility of the kernel and the femoral head), while the second type of insert can give single mobility (mobility of the femoral head).

If the system is eccentric, it is observed that this eccentricity can lateralise the prosthetic assembly.

The internal hemispherical cavity of the mobile kernel may also be made eccentric from the axis of symmetry.

According to another characteristic, the second type of insert and the mobile kernel are provided with arrangements for the assembly of a ring to assure that the femoral head is retained.

This ring is split so that it can be moved apart elastically to be positioned in complementary shaped arrangements at the opening of the insert or the kernel. The ring delimits a concave internal contact surface related to the hemispherical external contact surface of the femoral head.

The arrangements of the internal layer of the cavity cooperate with complementary arrangements on the outside surface of the two types of inserts to solve the problem that arises to fix each of the insert types into the metallic cup, and thus particularly to make a fixation by a clipping effect.

Advantageously, the arrangements are composed of a series of truncated circular contact surfaces.

Starting from this basic concept, the first type of insert is made of ceramic, polyethylene or metal, while the second type of insert is either ceramic, polyethylene or metal. The kernel itself is either ceramic, polyethylene or metal.

In one advantageous embodiment, the inserts, kernel and the femoral head are made of ceramic.

The first and second types of inserts and the kernel are made either of metal, or polyethylene or ceramic, or a combination of these materials, the femoral head being made either of metal or ceramic or a combination of these materials.

Similarly, it is perfectly possible that these three elements could be made of polyethylene, except for the femoral head. Thus, inserts of the first and second types and the kernel and the femoral head are made either of metal, or polyethylene or ceramic, or a combination of these materials.

The invention is described below in more detail with reference to the Figures in the appended drawings in which:

BRIEF DESCRIPTION OF THE DRAWINGS

FIG. 1*bis* is similar to FIG. 1 in which the internal hemispherical cavity of the mobile kernel is eccentric from the axis of symmetry;

DETAILED DESCRIPTION OF THE INVENTION

According to the invention, the acetabular implant comprises a common hemispherically shaped metallic cup (1). This cup (1) is provided with all necessary arrangements so that it can be fixed in the acetabular cavity of the iliac bone with or without cement. This cup (1) delimits an internal cavity (1a) with arrangements so that the surgeon can choose to install one of two types of inserts (2) or (3).

The choice of the insert type (2) or (3) depends on the desire and the need to increase the head diameter and/or to obtain double mobility or single mobility.

The first type of insert (2) is provided with a spherical internal cavity (2a) for assembly of a hemispherical kernel (4), with freedom to move, the kernel having a hemispherical concave internal cavity (4a) for assembly of a femoral head (T) as provided on the corresponding femoral implant, with an articulation capability. In this embodiment shown in FIGS. 1 to 3 and 4, double mobility is obtained by the multidirectional displacement capability of the kernel (4) in the cavity (2a) of the insert (2) and the femoral head (T) being in the internal cavity (4a) of the kernel (4).

Figure 1:
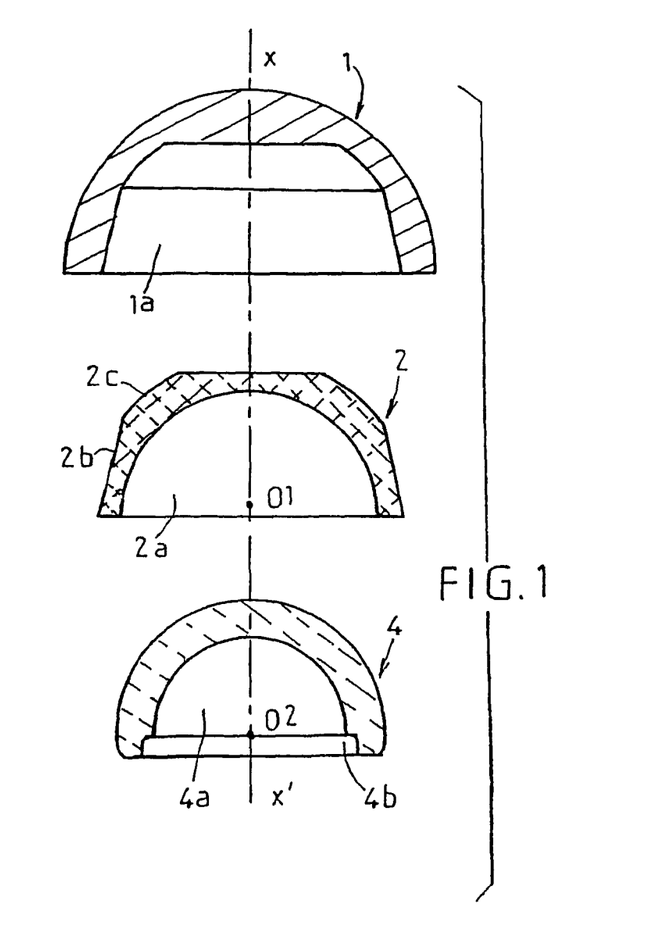
FIG. 1 shows a longitudinal sectional view before assembly of components of the acetabular implant, in the case in which the implant is of the first type for assembly with freedom of the kernel that will hold the femoral head to move, in the case of an alignment of different centres with respect to the axis of symmetry of the cup.
Figure 2:
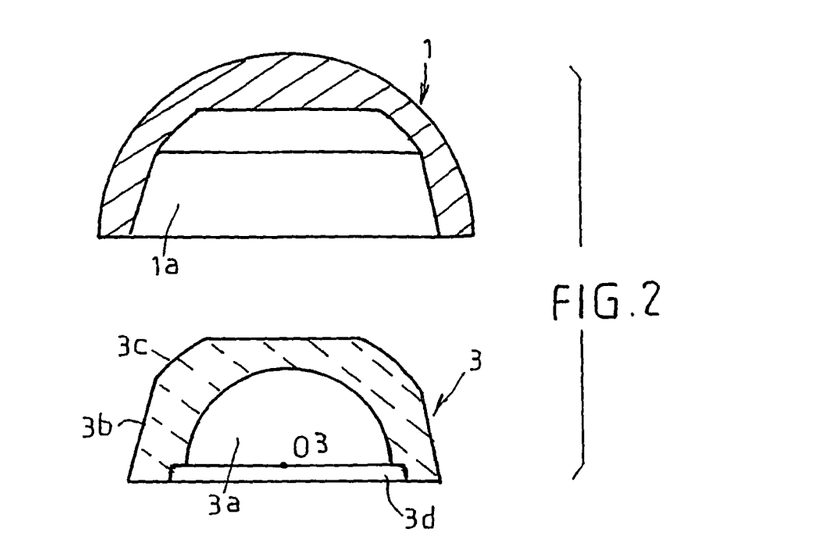
FIG. 2 is a longitudinal sectional view before assembly of the main components of the acetabular implant, in the case of the second type of insert that will hold the femoral head directly, and in the case in which the different centres are in line with the axis of symmetry of the cup.
Figure 3:
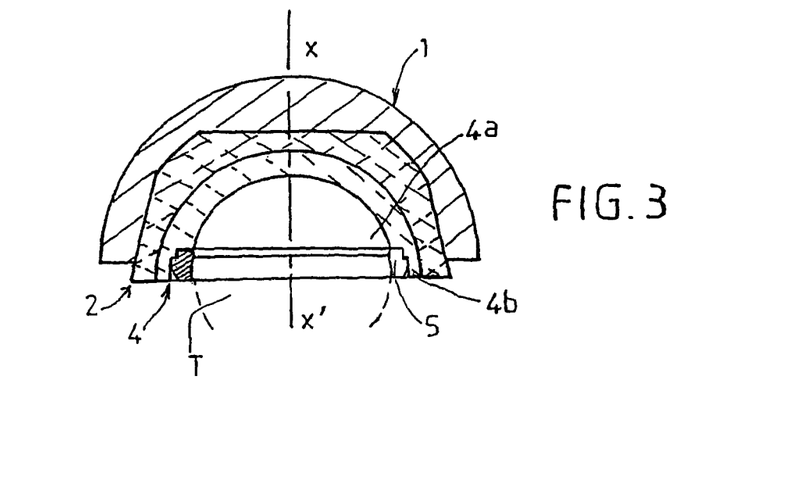
FIG. 3 is a longitudinal sectional view of the assembly of the acetabular implant according to the embodiment in FIG. 1.
Figure 4:
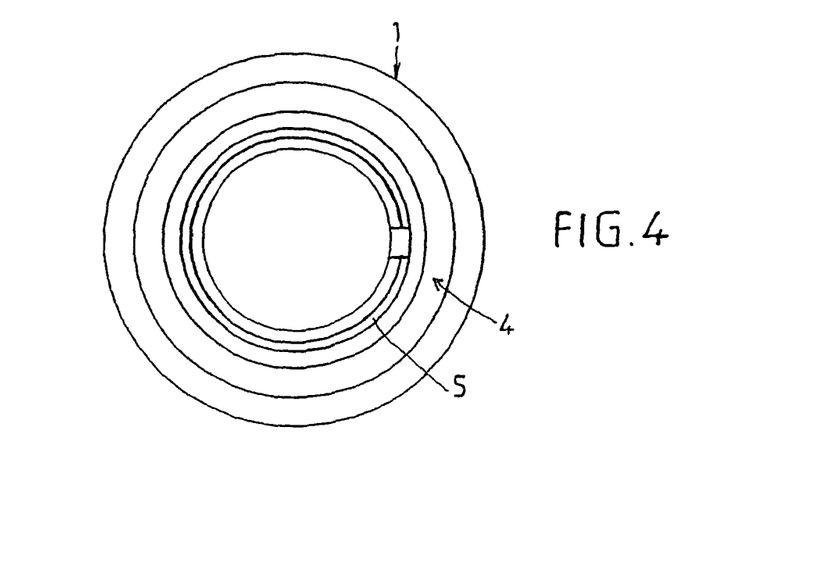
FIG. 4 is a bottom view corresponding to FIG. 3.
Figure 5:
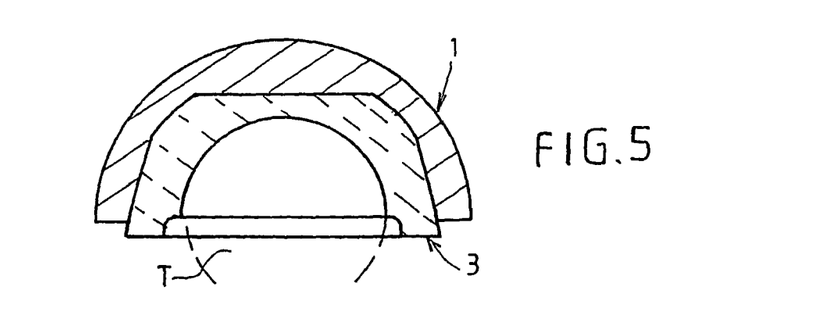
FIG. 5 is a longitudinal sectional view of the acetabular implant assembly according to the illustrated embodiment in FIG. 2.
Figure 6:
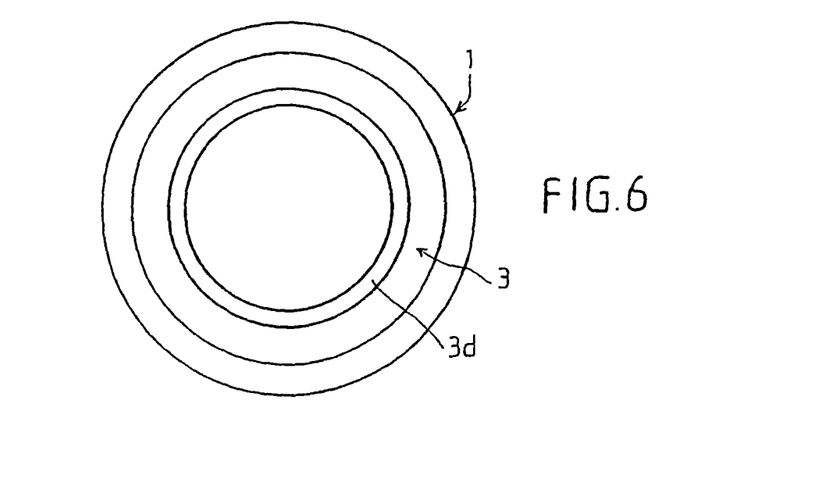
FIG. 6 is a bottom view corresponding to FIG. 5.
Figure 7:
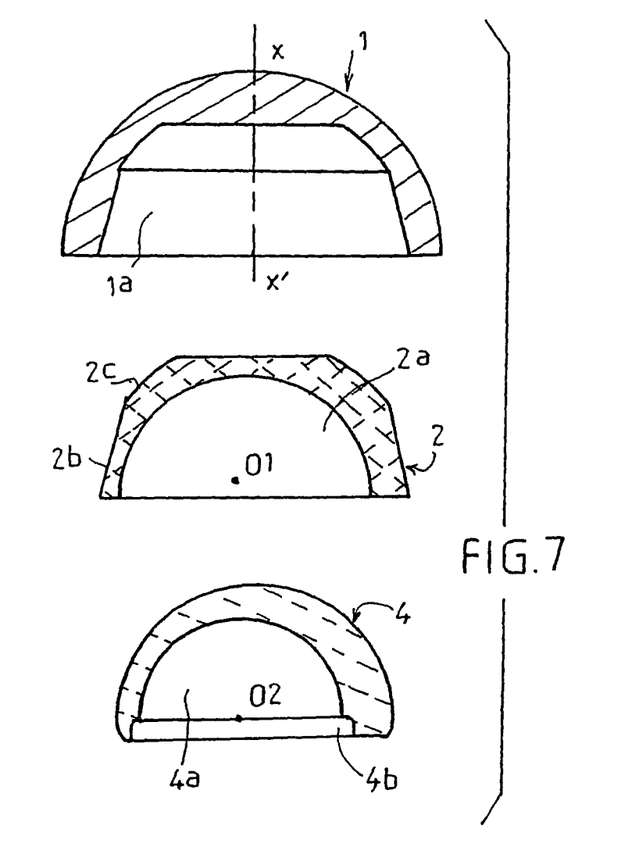
FIG. 7 is a longitudinal sectional view before assembly of components of the acetabular implant, in the case in which the insert is of the first type for assembly with freedom to move of a kernel that will contain the femoral head and in the case in which the centres of rotation are offset from the axis of symmetry of the cup.
Figure 8:
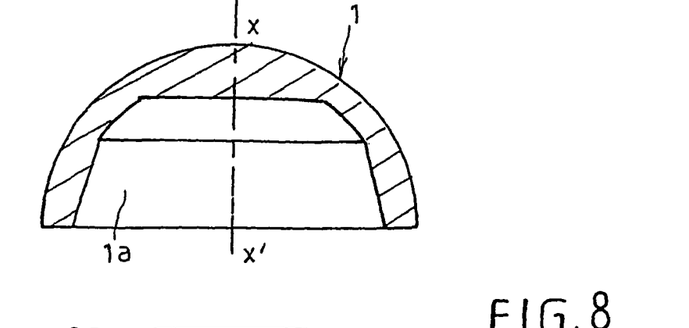
FIG. 8 is a longitudinal sectional view before assembly of the main components of the acetabular implant, in the case of an insert of the second type into which the femoral head will fit directly and if the centres are offset from the axis of symmetry of the cup.
Figure 9:
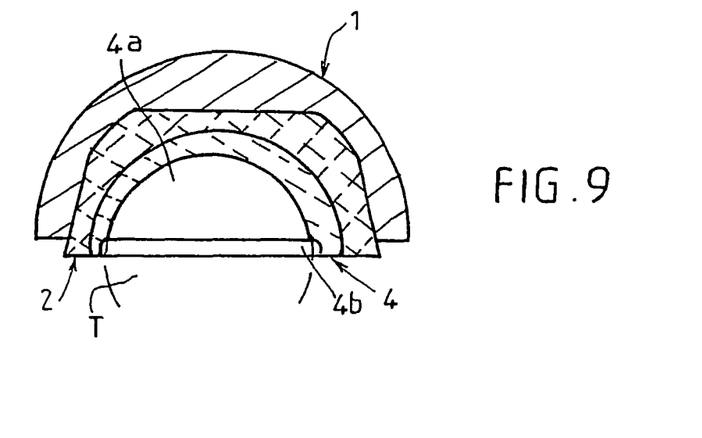
FIG. 9 is a longitudinal sectional view of the acetabular implant assembly according to the embodiment in FIG. 7.
Figure 10:
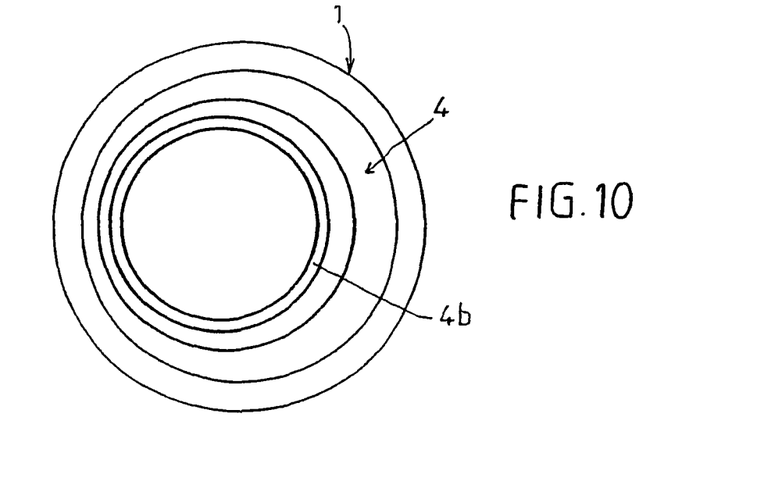
FIG. 10 shows a bottom view corresponding to FIG. 9.
Figure 11:
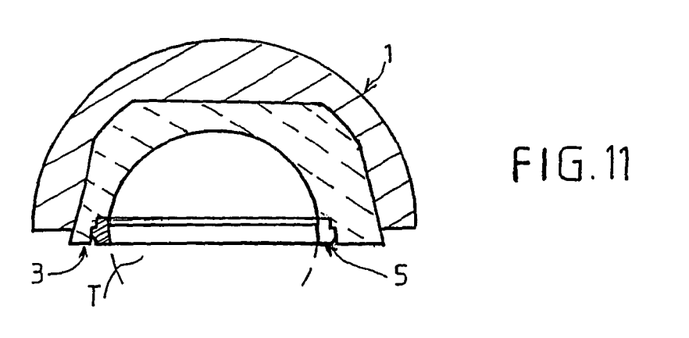
FIG. 11 is a longitudinal sectional view of the acetabular implant assembly according to the embodiment illustrated in FIG. 8.
Figure 12:
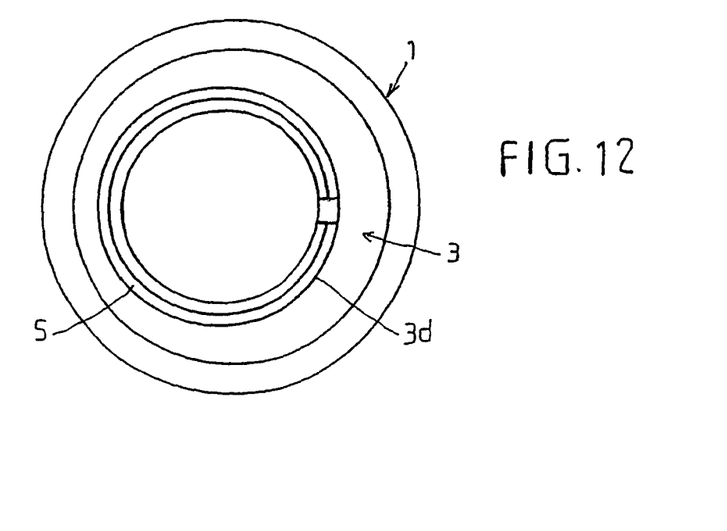
FIG. 12 shows a bottom view corresponding to FIG. 11.

The second type of insert (3) has an internal cavity (3a) capable of cooperating with the femoral head (T) with an articulation capability. According to this embodiment shown in FIGS. 2, 5 and 6, mobility is achieved by multidirectional displacement of the head (T) in the cavity (3a) of the insert (3).

Figure 13:
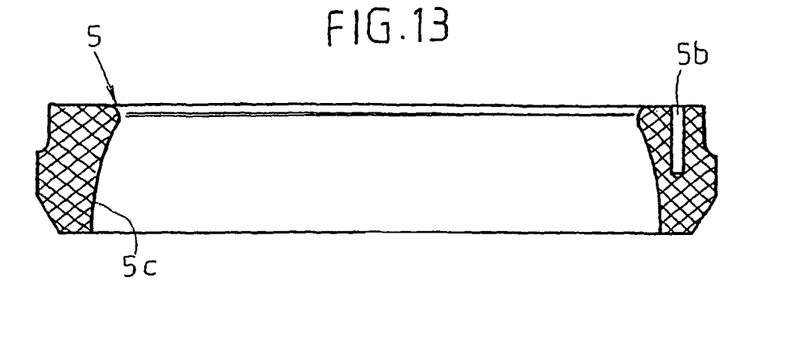
FIG. 13 shows a longitudinal sectional view of the retention ring alone at a larger scale.
Figure 14:
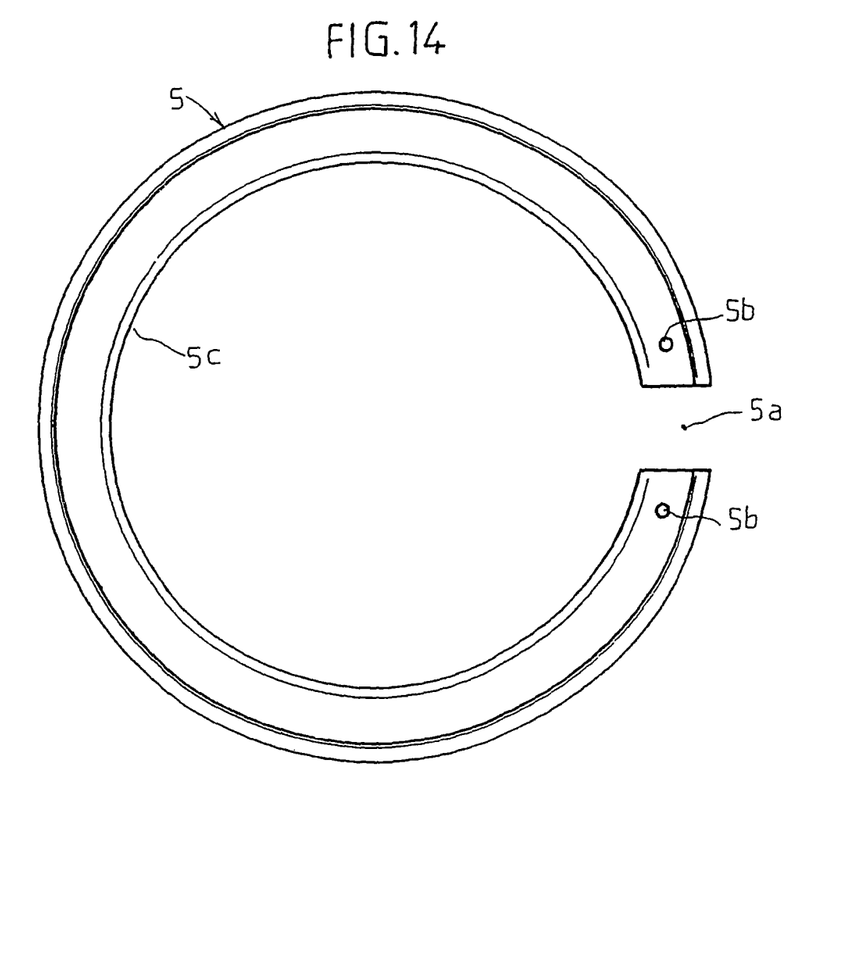
FIG. 14 shows a top view corresponding to FIG. 13.

Note that the second type of insert (3) (and possibly the insert (2)) and the mobile kernel (4) may be provided with arrangements (3d) and (4b) for assembly of a ring (5) to retain the femoral head (T). For example, a staged circular contact surface is formed concentrically with cavities (3a) and (4a), the circular contact surface having a greater diameter than the said cavities. The ring (5) has an external profile conform with the profile illustrated in FIG. 13 and is split at (5a) to be moved apart elastically so that it can be put into place at the staged circular contact surfaces (3d) and (4b). The parts of a clamp are inserted in the holes (5b). The internal contact surface (5c) of the ring (5) is concave in relation to the external hemispherical contact surface of the femoral head (T). The ring provides a retentive effect, in other words it maintains the femoral head in the inserts between the femoral head and the bottom of the cavity of the mobile kernel (4).

It can also be seen that the diameters of the cavities (3a) and (4a) are identical to hold the same femoral head (T) with a determined diameter. Obviously the diameters of the cavities (3a) and (4a) are determined for a dimensional range corresponding to the diameters of the femoral heads (T)

The internal cavity (1a) of the cup (1) is provided with arrangements for fixed assembly of either of the insert types (2) and (3). To achieve this, these arrangements cooperate with complementary arrangements on the outside face of the insert (2) and the insert (3) particularly for fixation by a clipping effect. To achieve this, in the embodiment illustrated these arrangements consist of a series of truncated circular contact surfaces (2b) and (2c) for an insert (2) and a series of truncated circular contact surfaces (3b) and (3c) for the insert (3).

Obviously, without going outside the scope of the invention, the insert (2) or the insert (3) could be fixed in the internal cavity (1a) of the cup (1) by other complementary assembly forms and by any known and appropriate means.

Advantageously, the first type of insert (2) is made of ceramic, while the second type of insert (3) is made of ceramic and the kernel (4) is also made of ceramic. Similarly, the metallic cup (1) may be provided with any coating and/or treatment of the outside surface.

Starting from this basic concept, in one preferred embodiment the insert, the mobile kernel and the femoral head are all made of ceramic.

The acetabular implant (first or second type of inserts, the kernel and possibly the femoral head) could also be fully metallic.

Considering the basic characteristics of the invention, the centres (O1) of the first type of insert (2), (O2) of the kernel (4) and (O3) of the second type of insert (3) are aligned with each other and along an axis of symmetry (x-x') of the cup (1) (FIGS. 1 to 6). Or the centres (O1) of the first type of insert (2), (O2) of the kernel (4) and (O3) of the second type of insert (3) are aligned and offset from the axis of symmetry (x-x') of the cup (1), to enable lateral assembly of the acetabular implant (FIGS. 7 to 12).

As shown in FIG. 1*bis*, it will also be possible to offset the internal cavity (4a) from the mobile kernel (4) along the axis of symmetry (x-x').

The main purpose of this invention is to improve prevention of the risk of luxations in hip prostheses in systems according to prior art. Furthermore, other advantages of the invention include the use of two insert types to obtain an assembly with double freedom to move with an intermediate kernel or single freedom to move without an intermediate kernel.

This double freedom to move also reduces risks of luxation and prevents conflict by providing automatic recentring.

Note that in the appended figures, the inserts are protuberant from the metallic cup. Nevertheless, it should be understood that this type of embodiment is not necessary and the device according to the invention will operate equally well.

The invention claimed is:

1. An acetabular implant for hip prosthesis, comprising:
    a metallic hemispherical shaped cup (1) structured to be fixed to the bottom of an acetabular cavity of an iliac bone, said cup having an axis of symmetry (x-x');
    an insert (2); and
    a hemispherical kernel (4),
    said cup (1) having an internal cavity (1a) adapted for receiving said insert (2),
    said insert (2) having a spherical internal cavity (2a) for receiving an assembly of said hemispherical kernel (4) having universal movement, and
    said hemispherical kernel (4) having an internal cavity (4a) adapted to cooperate with a femoral head (T) with an articulation capability,
    wherein the spherical internal cavity (2a) of the insert (2) and the internal spherical cavity (4a) of said hemispherical kernel (4) have respectively a center of rotation (01, 02), the respective centers of rotation (01, 02) being aligned on the axis of symmetry (x-x') of the cup, and being non-coincident when the cup (1), insert (2) and kernel (4) are assembled.

2. Implant according to claim 1, wherein the internal cavity (1a) of the cup (1) is provided with arrangements for assembly at will, in a fixed manner, of the insert (2).

3. Implant according to claim 2, wherein the mobile kernel (4) is provided with arrangements for the assembly of a ring (5) to assure that the femoral head is retained.

4. Implant according to claim 3, wherein the ring (5) is split so that it can be moved apart elastically to be positioned in complementary shaped arrangements at the opening of the kernel, the ring delimiting a concave internal contact surface with the hemispherical external contact surface of the femoral head.

5. Implant according to claim 4, wherein the arrangements of the internal cavity (1a) of the cup (1) cooperate with complementary arrangements on the outside surface of the insert (2) to make a fixation by a clipping effect.

6. Implant according to claim 5, wherein the arrangements are composed of a series of truncated circular contact surfaces.

7. Implant according to claim 6, wherein the insert (2) and the kernel (4) are made of one of ceramic, polyethylene and metal, and the femoral head is made of one of ceramic and metal.

8. Implant according to claim 7, wherein the insert (2) and the kernel (4) are made of one of i) metal, ii) polyethylene, iii) ceramic, and iv) a combination of metal, polyethylene, and ceramic, and the femoral head is made of one of metal, ceramic, and a combination of metal and ceramic.

9. Implant according to claim 1, wherein the mobile kernel (4) is provided with arrangements for the assembly of a ring (5) to assure that the femoral head is retained.

10. Implant according to claim 9, wherein the ring (5) is split to be moved apart elastically to be positioned in complementary shaped arrangements at the opening of the kernel, the ring delimiting a concave internal contact surface with the hemispherical external contact surface of the femoral head.

11. Implant according to claim 2, wherein the arrangements of the internal cavity (1a) of the cup (1) cooperate with complementary arrangements on the outside surface of the insert (2) to make a fixation by a clipping effect.

12. Implant according to claim 11, wherein the arrangements are composed of a series of truncated circular contact surfaces.

13. Implant according to claim 1, wherein the insert (2) and the kernel (4) are made of one of ceramic, polyethylene and metal, and the femoral head is made of one of ceramic and metal.

14. Implant according to claim 1, wherein the insert (2) and the kernel (4) are made of one of i) metal, ii) polyethylene, iii) ceramic, and iv) a combination of metal, polyethylene, and ceramic, and the femoral head is made of one of metal, ceramic, and a combination of metal and ceramic.

15. An acetabular implant for hip prosthesis, comprising:
    a metallic hemispherical shaped cup (1) structured to be fixed to the bottom of an acetabular cavity of an iliac bone, said cup having an axis of symmetry (x-x');
    an insert (2); and
    a hemispherical kernel (4),
    said cup (1) having an internal cavity (1a) adapted for receiving said insert (2),
    said insert (2) having a spherical internal cavity (2a) for receiving an assembly of said hemispherical kernel (4) having universal movement, and
    said hemispherical kernel (4) having an internal cavity (4a) adapted to cooperate with a femoral head (T) with an articulation capability,
    wherein the spherical internal cavity (2a) of the insert (2) and the internal spherical cavity (4a) of said hemispherical kernel (4) have respectively a center of rotation (01, 02), the respective centers of rotation (01, 02) being aligned on the axis of symmetry (x-x') of the cup, and being non-coincident when the cup (1), insert (2) and kernel (4) are assembled, said kernel being in direct contact with said insert.

* * * * *

UNITED STATES PATENT AND TRADEMARK OFFICE
CERTIFICATE OF CORRECTION

PATENT NO.        : 8,529,633 B2                                                           Page 1 of 1
APPLICATION NO. : 10/541680
DATED             : September 10, 2013
INVENTOR(S)       : Lazennec et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this

Fifteenth Day of September, 2015

Michelle K. Lee
*Director of the United States Patent and Trademark Office*